(12) United States Patent
Nesvadba et al.

(10) Patent No.: US 7,723,399 B2
(45) Date of Patent: May 25, 2010

(54) N-SUBSTITUTED IMIDES AS POLYMERIZATION INITIATORS

(75) Inventors: Peter Nesvadba, Marly (CH); Johannes Benkhoff, Basel (CH); Lucienne Bugnon, Pfeffingen (CH); Karin Powell, Lörrach (DE); Tunja Jung, Rheinfelden-Herten (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 185 days.

(21) Appl. No.: 11/666,887

(22) PCT Filed: Oct. 31, 2005

(86) PCT No.: PCT/EP2005/055646
§ 371 (c)(1),
(2), (4) Date: May 1, 2007

(87) PCT Pub. No.: WO2006/051047
PCT Pub. Date: May 18, 2006

(65) Prior Publication Data
US 2008/0132600 A1 Jun. 5, 2008

(30) Foreign Application Priority Data
Nov. 9, 2004 (EP) .................................. 04105620

(51) Int. Cl.
C08F 299/00 (2006.01)
C07D 221/04 (2006.01)
C07D 209/56 (2006.01)
C07D 209/48 (2006.01)

(52) U.S. Cl. ..................... 522/167; 522/176; 548/435; 548/475; 548/542; 546/335; 546/99; 558/234; 524/609; 524/612

(58) Field of Classification Search ................ 522/167, 522/176, 234; 546/335, 99; 558/168, 234; 548/475, 542, 435; 524/612, 609
See application file for complete search history.

(56) References Cited

U.S. PATENT DOCUMENTS

| | | | |
|---|---|---|---|
| 2,872,450 A | 2/1959 | Sasse et al. | 260/281 |
| 3,928,493 A | 12/1975 | MacLeay et al. | 260/864 |
| 4,966,923 A * | 10/1990 | Banks et al. | 522/167 |
| 2003/0204034 A1 | 10/2003 | Charmot et al. | 526/220 |
| 2004/0147437 A1 | 7/2004 | Findlay | 514/12 |

FOREIGN PATENT DOCUMENTS

WO 02/15939 2/2002

OTHER PUBLICATIONS

Li et al.; Journal of Peptide Research, vol. 58(2) (2001) pp. 129-139 (XP 001039108).
Chinchilla et al.; Arkivoc 2003(x) pp. 41-47 (XP-002368296).
Abajo et al.; Anales De Quimica, vol. 70, 1974; pp. 908-913 (XP 009062111).
Database Beilstein, RN 6932217 (XP-002368473).
Nakano et al.; J. Org. Chem. vol. 40, No. 15, (1975) pp. 2215-2220.

* cited by examiner

*Primary Examiner*—Mark Eashoo
*Assistant Examiner*—Jessica Paul
(74) *Attorney, Agent, or Firm*—Jospeh C. Suhadolnik

(57) ABSTRACT

The invention relates to novel N-substituted imides and polymerizable compositions comprising these N-substituted imides. The invention further relates to the use of N-substituted imides as polymerization initiators. The imides are compounds of the formula (I) and (II) wherein n is 1 or 2; m is 1 or 2; $R_1$ and $R_2$ are each, independently of one another, hydrogen, $C_1$-$C_{18}$alkyl, $C_1$-$C_{18}$alkenyl $C_6$-$C_{14}$aryl, aralkyl, $C_5$-$C_{12}$cycloalkyl, each of which may be substituted by halogen, $C_1$-$C_4$-alkyl, hydroxy, $C_1$-$C_6$alkoxy, carbonyl, $C_1$-$C_6$alkoxycarbonyl; or $R_1$ and $R_2$ together with the adjacent —CO—N—CO— group may form a monocyclic, bicyclic or polycyclic ring, said ring having up to 50 non hydrogen atoms and wherein said ring may contain the structural element (formula III) more than once; $R_3$ if n is 1, is $C_1$-$C_{18}$alkyl, $C_6$-$C_{14}$aryl, aralkyl, $C_5$-$C_{12}$cycloalkyl, $OR_{10}$ or $SR_{11}$, $NR_{12}R_{13}$; wherein $R_3$ if n is 2, is $C_2$-$C_{12}$alkylene, $C_6$-$C_{14}$arylene, xylylene $R_4$ and $R_5$, correspond to $R_1$ and $R_2$; $R_6$ if n is 1, is hydrogen, $C_1$-$C_{18}$alkyl, $C_6$-$C_{14}$aryl, aralkyl, $C_5$-$C_{12}$cycloalkyl, $NR_{14}R_{15}$; wherein $R_6$ if n is 2, is $C_2$-$C_{12}$alkylene, $C_6$-$C_{14}$arylene, xylylene; $R_7$ is hydrogen, $C_1$-$C_{18}$alkyl, $C_6$-$C_{14}$aryl, aralkyl, $C_5$-$C_{12}$cycloalkyl, each of which may be substituted by halogen, $C_1$-$C_4$-alkyl, hydroxy, $C_1$-$C_6$alkoxy, carbonyl, $C_1$-$C_6$alkoxy-carbonyl; or $R_7$ and $R_{14}$ or $R_7$ and $R_{15}$ form together with the N-atom attached to $R_7$ a 5-6 membered ring, optionally interrupted by —NH—, —N($C_1$-$C_8$alkyl)-, —O— and/or S-atoms.

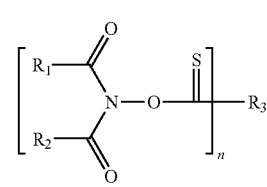

(I)

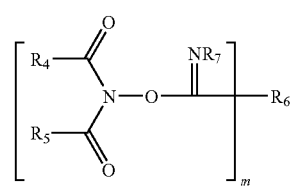

(II)

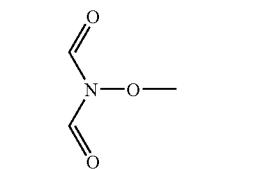

(III)

7 Claims, No Drawings

N-SUBSTITUTED IMIDES AS POLYMERIZATION INITIATORS

The invention relates to novel N-substituted imides and polymerizable compositions comprising these N-substituted imides. The invention further relates to the use of N-substituted imides as polymerization initiators.

Free-radical polymerization is among the most important methods of building up a relatively long carbon chain. It is employed in process technology for preparing commercially important polymers such as polystyrene, PVC, poly(meth)acrylates, PAN and other polymers. For technical details, reference may be made to the still relevant standard work G. Odian, *Principles of Polymerization*, McGraw-Hill New York 1991.

Free-radical polymerizations are started using initiators. Initiators which have become established in process technology are azo compounds, dialkyl peroxides, diacyl peroxides, hydroperoxides, thermolabile C—C-dimers, redox systems and photoinitiators. Reference is made to the "Handbook of Free Radical Initiators", (E. T. Denisov, T. G. Denisova, T. S. Pokidova, J. Wiley & Sons, Inc. Hoboken, N.J., 2003).

Despite their widespread use, these initiators have various disadvantages. Thus, for example, peroxides are extremely readily ignitable and sustain fire. Other classes of substances are potential explosion hazards, so that their use, storage and transport has to involve costly safety precautions. Some initiators generate toxic products, as e.g. AIBN.

There is therefore a general need for advantageous initiators useful in process technology which have a satisfactory safety profile for free-radical polymerization processes.

J. D. Druliner describes in J. Phys. Org. Chem. 8, 316-324 (1995) the polymerization of acrylates and methacrylates to make homopolymers and block copolymers initiated by N-alkoxyphthalimides and succinimides.

U.S. Pat. No. 2,872,450 describes the manufacture of thio- and dithiocarboxylic acid esters by reaction of cyclic oximides and thio- or dithiocarboxylic acid ester chlorides and their use as fungicides.

U.S. Pat. No. 6,667,376 describes compounds of the general formula $R_1$—S—C(=S)—O—$NR_2R_3$ used as control agents for living type free radical polymerization.

It has been found that certain dicarboxylic acid imides are particularly suitable as polymerization initiators if they are esterified by thio-acyl-, or imino radicals.

The invention provides compounds of the formula I and II

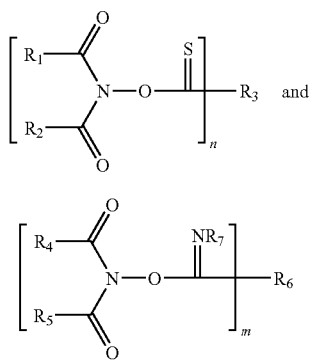

wherein
n is 1 or 2;
m is 1 or 2;

$R_1$ and $R_2$ are each, independently of one another, hydrogen, $C_1$-$C_{18}$alkyl, $C_1$-$C_{18}$alkenyl, $C_6$-$C_{14}$aryl, aralkyl, $C_5$-$C_{12}$cycloalkyl, each of which may be substituted by halogen, $C_1$-$C_4$-alkyl, hydroxy, $C_1$-$C_6$alkoxy, carbonyl, $C_1$-$C_6$alkoxycarbonyl; or $R_1$ and $R_2$ together with the adjacent —CO—N—CO— group may form a monocyclic, bicyclic or polycyclic ring, said ring having up to 50 non hydrogen atoms and wherein said ring may contain the structural element

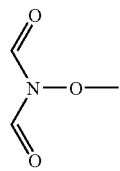

more than once;

$R_3$ if n is 1, is $C_1$-$C_{18}$alkyl, $C_1$-$C_{18}$alkenyl, $C_6$-$C_{14}$aryl, aralkyl, $C_5$-$C_{12}$cycloalkyl, each of which may be substituted by halogen, $C_1$-$C_4$-alkyl, hydroxy, $C_1$-$C_6$alkoxy, carbonyl, $C_1$-$C_6$alkoxycarbonyl; or $R_3$ is $OR_{10}$ or $SR_{11}$, $NR_{12}R_{13}$; wherein $R_{10}$ is $C_1$-$C_{18}$alkyl, $C_6$-$C_{14}$aryl, aralkyl, $C_5$-$C_{12}$cycloalkyl, each of which may be substituted by halogen, $C_1$-$C_4$-alkyl, hydroxy, $C_1$-$C_6$alkoxy, carbonyl, $C_1$-$C_6$alkoxycarbonyl; and $R_{11}$ is $C_1$-$C_{18}$alkyl, $C_6$-$C_{14}$aryl, aralkyl, $C_5$-$C_{12}$cycloalkyl, each of which may be substituted by halogen, $C_1$-$C_4$-alkyl, hydroxy, $C_1$-$C_6$alkoxy, carbonyl, $C_1$-$C_6$alkoxycarbonyl; and $R_{12}$ and $R_{13}$ independently of one another are hydrogen, $C_1$-$C_{18}$alkyl, $C_6$-$C_{14}$aryl, aralkyl, $C_5$-$C_{12}$cycloalkyl, each of which may be substituted by halogen, $C_1$-$C_4$-alkyl, hydroxy, $C_1$-$C_6$alkoxy, carbonyl, $C_1$-$C_6$alkoxycarbonyl; or $R_{12}$ and $R_{13}$ form together with the N atom to which they are attached a 5 or 6 membered ring, optionally interrupted by —NH—, —N($C_1$-$C_8$alkyl)-, —O— and/or S-atoms, $R_3$ if n is 2, is $C_2$-$C_{12}$alkylene, $C_2$-$C_{12}$alkenylene, $C_6$-$C_{14}$arylene, xylylene; with the proviso, that the following compounds disclosed in U.S. Pat. No. 2,872,450 as fungicides are excluded,

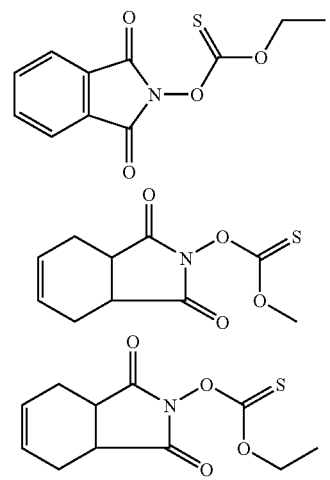

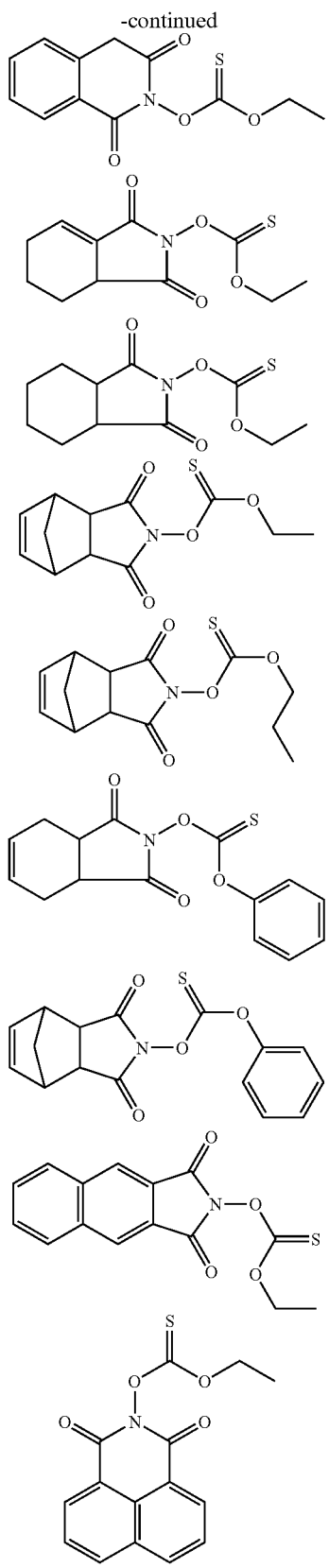

R$_4$ and R$_5$ are each, independently of one another, hydrogen, C$_1$-C$_{18}$alkyl, C$_1$-C$_{18}$alkenyl C$_6$-C$_{14}$aryl, aralkyl, C$_5$-C$_{12}$cycloalkyl, each of which may be substituted by halogen, C$_1$-C$_4$-alkyl, hydroxy, C$_1$-C$_6$alkoxy, carbonyl, C$_1$-C$_6$alkoxycarbonyl; or R$_4$ and R$_5$ together with the adjacent —CO—N—CO— group may form a monocyclic, bicyclic or polycyclic ring, said ring having up to 50 non hydrogen atoms and wherein said ring may contain the structural element

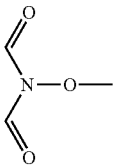

more than once;

R$_6$ if n is 1, is hydrogen, C$_1$-C$_{18}$alkyl, C$_1$-C$_{18}$alkenyl, C$_6$-C$_{14}$aryl, aralkyl, C$_5$-C$_{12}$cycloalkyl, each of which may be substituted by halogen, C$_1$-C$_4$-alkyl, hydroxy, C$_1$-C$_6$alkoxy, carbonyl, C$_1$-C$_6$alkoxycarbonyl; or R$_6$ is NR$_{14}$R$_{15}$; wherein R$_{14}$ and R$_{15}$ independently of one another are hydrogen, C$_1$-C$_{18}$alkyl, C$_6$-C$_{14}$aryl, aralkyl, C$_5$-C$_{12}$cycloalkyl, each of which may be substituted by halogen, C$_1$-C$_4$-alkyl, hydroxy, C$_1$-C$_6$alkoxy, carbonyl, C$_1$-C$_6$alkoxycarbonyl; or R$_{14}$ and R$_{15}$ form together with the N atom to which they are attached a 5 or 6 membered ring, optionally interrupted by —NH—, —N(C$_1$-C$_8$alkyl)-, —O— and/or S-atoms, R$_6$ if n is 2, is C$_2$-C$_{12}$alkylene, C$_2$-C$_{12}$alkenylene, C$_6$-C$_{14}$arylene, xylylene;

R$_7$ is hydrogen, C$_1$-C$_{18}$alkyl, C$_6$-C$_{14}$aryl, aralkyl, C$_5$-C$_{12}$cycloalkyl, each of which may be substituted by halogen, C$_1$-C$_4$-alkyl, hydroxy, C$_1$-C$_6$alkoxy, carbonyl, C$_1$-C$_6$alkoxycarbonyl; or R$_7$ and R$_{14}$ or R$_7$ and R$_{15}$ form together with the N-atom attached to R$_7$ a 5-6 membered ring, optionally interrupted by —NH—, —N(C$_1$-C$_8$alkyl)-, —O— and/or S-atoms.

Definitions

The term "C$_1$-C$_{18}$alkyl" includes, for example, C$_1$-C$_6$alkyl, e.g. methyl, ethyl, n-propyl or isopropyl or n-, sec- or tert-butyl or straight-chain or branched pentyl or hexyl, or C$_7$-C$_{18}$alkyl, e.g. straight-chain or branched heptyl, octyl, isooctyl, nonyl, tert-nonyl, decyl or undecyl, or straight-chain C$_{11}$-C$_{18}$alkyl, which together with the —(C═O)— radical forms C$_{14}$-C$_{20}$-alkanoyl having an even number of C-atoms, e.g. lauroyl (C12), myristoyl (C14), palmitoyl (C16) or stearoyl (C18).

The term "C$_1$-C$_{18}$alkenyl" means an unsaturated, linear or branched hydrocarbon group as defined above under alkyl with one or more carbon-carbon double bonds, such as a vinyl group.

The term "C$_2$-C$_{12}$alkylene" means a divalent group derived from a straight or branched chain hydrocarbon of from 1 to 12 carbon atoms. Examples of alkylene groups may include ethylene, propylene, 2,2-dimethylpropylene, tetramethylene, hexamethylene, octamethylene, decamethylene or dodecamethylene.

The term "C$_6$-C$_{14}$aryl" refers to an optionally substituted benzene ring or to an optionally substituted benzene ring fused to one or more optionally substituted benzene rings to form a ring system. Preferred aryl groups are phenyl, 2-naphthyl, tetrahydronaphthyl, 1-naphthyl, biphenyl, indanyl, anthracyl, phenanthryl, as well as substituted derivatives thereof. Examples of substituents are: C$_1$-C$_{18}$alkyl, $C_6$-$C_{14}$aryl, aralkyl, $C_5$-$C_{12}$cycloalkyl, halogen, OH, $C_1$-$C_{18}$alkoxy, $C_1$-$C_{18}$alkylthio, carboxy, $C_1$-$C_{18}$alkoxycarbonyl, carbamoyl (C(O)NH$_2$), $C_1$-$C_{18}$alkylcarbamoyl, di-$C_1$-$C_{18}$alkylcarbamoyl, acyl, nitro, amino, $C_1$-$C_{18}$alkylamino or di-$C_1$-$C_{18}$alkylamino, —CH$_2$—X—CH$_2$— wherein X is O, NH, N($C_1$-$C_{18}$alkyl).

The term "$C_6$-$C_{14}$arylene" refers to an optionally substituted benzene ring diradical or to a benzene ring system diradical containing an optionally substituted benzene ring fused to one or more optionally substituted benzene rings. Examples correspond to the aryl groups above.

The term "aralkyl" includes a radical RaRb, where Ra is an alkylene (a bivalent alkyl) group and Rb is an aryl group as defined above. Preferred are $C_7$-$C_8$aralkyl groups such as 2-phenylethyl or benzyl.

The term "$C_5$-$C_{12}$cycloalkyl" includes a monovalent, alicyclic, saturated hydrocarbon radical having three or more carbon atoms forming the ring. While the cycloalkyl compounds may have up to 12 carbon atoms, generally there will be three to seven carbon atoms in the ring. The latter include, for example, cyclopropyl, cyclobutyl, cyclopentyl, cyclohexyl, and cycloheptyl.

The term "monocyclic ring" includes a 5 to 9 membered ring system such as, for example, dioxo pyrrolidine, dioxo piperidine, dioxo morpholine, dioxo thiomorpholine or a derivative derived from trihydroxyisocyanuric acid, The monocyclic ring system is preferably a residue of the formula,

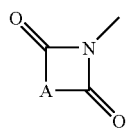

wherein A is unsubstituted ethylene or propylene, ethylene or propylene substituted by $C_1$-$C_{18}$alkyl, $C_6$-$C_{14}$aryl, aralkyl, $C_5$-$C_{12}$cycloalkyl, halogen, OH, $C_1$-$C_{18}$alkoxy, $C_1$-$C_{18}$alkylthio, carboxy, $C_1$-$C_{18}$alkoxycarbonyl, carbamoyl (C(O)NH$_2$), $C_1$-$C_{18}$alkylcarbamoyl, di-$C_1$-$C_{18}$alkylcarbamoyl, acyl, nitro, amino, $C_1$-$C_{18}$alkylamino or i-$C_1$-$C_{18}$alkylamino, —CH$_2$—X—CH$_2$— wherein X is O, NH, N($C_1$-$C_{18}$alkyl); or —N(OH)—CO—N(OH)—.

A monocyclic ring derived from trihydroxyisocyanuric acid is e.g.

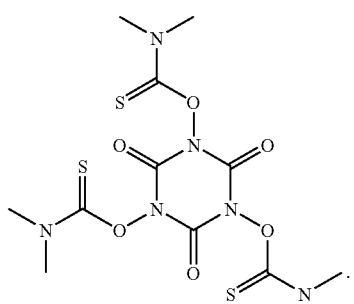

The term "acyl" refers to the group RaC(O)—, where Ra is $C_1$-$C_{18}$alkyl, $C_5$-$C_{12}$cycloalkyl, or heterocyclyl as defined herein. Examples of "heterocyclic" moieties include, for example, tetrahydrofuran, pyran, 1,4-dioxane, 1,3-dioxane, piperidine, pyrrolidine, morpholine, tetrahydrothiopyran, tetrahydrothiophene.

The term "bicyclic ring" means a 5 to 12 membered fused ring system.

The term "fused ring system" pertains to a system comprising in addition to the monocyclic core ring defined above, one or more aromatic rings, or one or more aliphatic rings. The aromatic ring as well as the aliphatic ring may comprise solely carbon atoms, or may comprise carbon atoms and one or more heteroatoms, including nitrogen, oxygen, and sulfur atoms. The aromatic ring is preferably a benzene ring resulting in dioxo-dihydro-isoindol rings or a naphthene ring resulting in dioxo-benzoisoquinoline rings. The aliphatic ring is e.g. an $C_3$-$C_7$cycloalkylene ring, an oxirane ring, a cyclohexenyl ring or a norbornene ring or bicyclo[2.2.2]octane or bicyclo[3.2.1]octane, or a group of the form

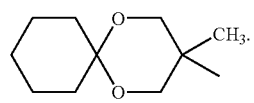

The aromatic ring(s) may optionally be substituted by substituted by $C_1$-$C_{18}$alkyl, $C_6$-$C_{14}$aryl, aralkyl, $C_5$-$C_{12}$cycloalkyl, halogen, OH, $C_1$-$C_{18}$alkoxy, $C_1$-$C_{18}$alkylthio, carboxy, $C_1$-$C_{18}$alkoxycarbonyl, carbamoyl (C(O)NH$_2$), $C_1$-$C_{18}$alkylcarbamoyl, di-$C_1$-$C_{18}$alkylcarbamoyl, acyl, nitro, amino, $C_1$-$C_{18}$alkylamino or di-$C_1$-$C_{18}$alkylamino, —CH$_2$—X—CH$_2$— wherein X is O, NH, N($C_1$-$C_{18}$alkyl).

The bicyclic ring system is preferably a residue of the formula

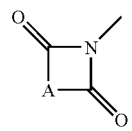

wherein A is phenylene, cyclohexylene, cyclohexenylene, 1,8-naphthylene, pyridinylene or wherein A is ethylene or propylene or ethylene or propylene substituted $C_1$-$C_4$alkyl, or ethenylene or propenylene or ethenylene or propenylene substituted $C_1$-$C_4$alkyl.

The term "polycyclic ring system" refers to ring systems having more than two cyclic compounds bonded. A polycyclic ring system as used herein may be aromatic or nonaromatic, or may be composed of separate aromatic and nonaromatic moieties. An example is adamantane or 1,3,5,7-tetra-aza-adamantane (urotropine), cubane, twistane, Polycyclic ring systems are also compounds of the formula I' and II'

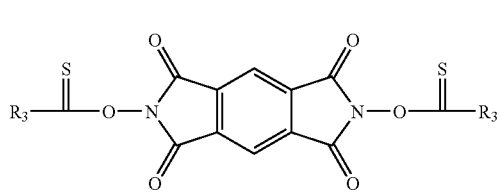

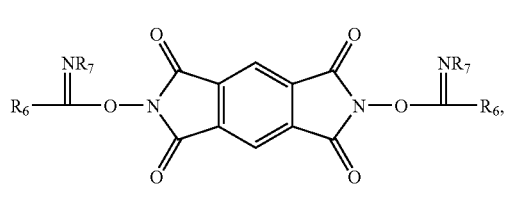

wherein $R_3$, $R_6$ and $R_7$ are as defined above.

Further examples of polycyclic residues may be:

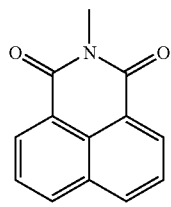

derived from 1,8 naphthalene dicarboxylic acid imide

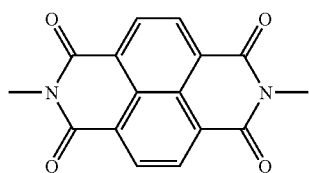

derived from naphthalene-1,4,5,8-tetracarboxylic acid diimide

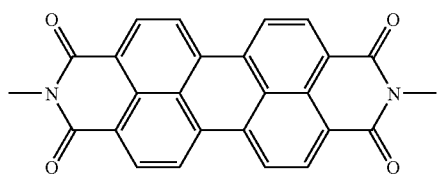

derived from 3,4,9,10-perylene tetracarboxylic acid diimide

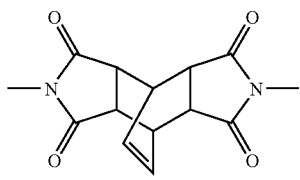

derived from bicyclo[2.2.2]oct-7-ene-2,3,5,6-tetracarboxylic acid diimide

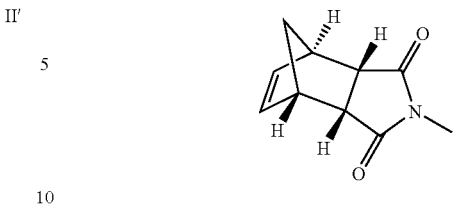

derived from 5-norbornene-2,3-dicarboxylic acid imide.

The term "non hydrogen atoms" includes C-Atoms and hetero atoms like N, S, O and P atoms.

When $R_{12}$ and $R_{13}$ or $R_{14}$ and $R_{15}$ or $R_7$ and $R_{14}$ or $R_7$ and $R_{15}$ together with the nitrogen atom to which they are attached, form a 5- or 6-membered ring that in addition may be interrupted by —NH—, —N($C_1$-$C_8$alkyl)-, —O— and/or S-atoms, the ring is, for example, a saturated or unsaturated ring, for example aziridine, piperazine, pyrrole, thiophene, pyrrolidine, oxazole, pyridine, 1,3-diazine, 1,2-diazine, piperidine or morpholine; morpholinyl, piperidyl or piperazinyl rings, especially, are formed.

Preferences

Preferred are compounds of the formula I and II, wherein $R_1$ and $R_2$ and $R_3$ and $R_4$ together with the adjacent —CO—N—CO— group form a monocyclic, bicyclic or polycyclic ring, resulting in compounds of the formula

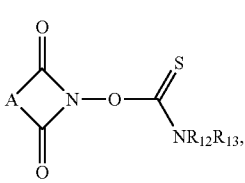

(Ia)

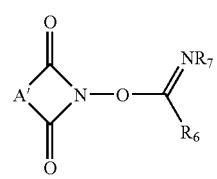

(IIa)

wherein

A is unsubstituted ethylene or propylene, ethylene or propylene substituted by $C_1$-$C_{18}$alkyl, $C_6$-$C_{14}$aryl, aralkyl, $C_5$-$C_{12}$cycloalkyl, halogen, OH, $C_1$-$C_{18}$alkoxy, $C_1$-$C_{18}$alkylthio, carboxy, $C_1$-$C_{18}$alkoxycarbonyl, carbamoyl (C(O)NH$_2$), $C_1$-$C_{18}$alkylcarbamoyl, di-$C_1$-$C_{18}$alkylcarbamoyl, acyl, nitro, amino, $C_1$-$C_{18}$alkylamino or di-$C_1$-$C_{18}$alkylamino; or A is ethenylene or propenylene or ethenylene or propenylene substituted $C_1$-$C_4$alkyl; or A is —CH$_2$—X—CH$_2$— wherein X is O, NH, N($C_1$-$C_{18}$alkyl); or —N(OH)—CO—N(OH)—; or A together with the adjacent —CO—N—CO— group may form a bicyclic or polycyclic ring, said ring having up to 20 non hydrogen atoms, and wherein said ring may contain the structural element

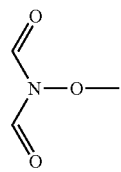

more than once;

$R_{12}$ and $R_{13}$ independently of one another are hydrogen, $C_1$-$C_{18}$alkyl, cyclohexyl, phenyl, benzyl, or $R_{12}$ and $R_{13}$ form together with the N atom to which they are attached a 5 or 6 membered ring, optionally interrupted by —NH—, —N($C_1$-$C_8$alkyl)-, —O— and/or S-atoms, A' is unsubstituted ethylene or propylene, ethylene or propylene substituted by $C_1$-$C_{18}$alkyl, $C_6$-$C_{14}$aryl, aralkyl, $C_5$-$C_{12}$cycloalkyl, halogen, OH, $C_1$-$C_{18}$alkoxy, $C_1$-$C_{18}$alkylthio, carboxy, $C_1$-$C_{18}$alkoxycarbonyl, carbamoyl (C(O)NH$_2$), $C_1$-$C_{18}$alkylcarbamoyl, di-$C_1$-$C_{18}$alkylcarbamoyl, acyl, nitro, amino, $C_1$-$C_{18}$alkylamino or di-$C_1$-$C_{18}$alkylamino; or A' is ethenylene or propenylene or ethenylene or propenylene substituted $C_1$-$C_4$alkyl; or A' is —CH$_2$—X—CH$_2$— wherein X is O, NH, N($C_1$-$C_{18}$alkyl); or —N(OH)—CO—N(OH)—. or A' together with the adjacent —CO—N—CO— group may form a bicyclic or polycyclic ring, said ring having up to 20 non hydrogen atoms, and wherein said ring may contain the structural element

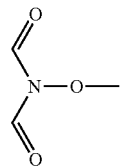

more than once;

$R_6$ is hydrogen, $C_1$-$C_{18}$alkyl, cyclohexyl, phenyl, benzyl, NR$_{14}$R$_{15}$; wherein $R_{14}$ and $R_{15}$ independently of one another are hydrogen, $C_1$-$C_{18}$alkyl, cyclohexyl, phenyl or $R_{14}$ and $R_{15}$ form together with the N atom to which they are attached a 5 or 6 membered ring, optionally interrupted by —NH—, —N($C_1$-$C_8$alkyl)-, —O— and/or S-atoms, $R_7$ is hydrogen, $C_1$-$C_{18}$alkyl, cyclohexyl, phenyl; or $R_7$ and $R_{14}$ or $R_7$ and $R_{15}$ form together with the N-atom attached to $R_7$ a 5-6 membered ring, optionally interrupted by —NH—, —N($C_1$-$C_8$alkyl)-, —O— and/or S-atoms.

Compounds of the formula I and II, wherein $R_1$ and $R_2$ and $R_3$ and $R_4$ together with the adjacent —CO—N—CO— group form a bicyclic ring resulting in compounds of the formula Ib and IIb

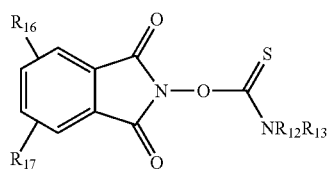
(Ib)

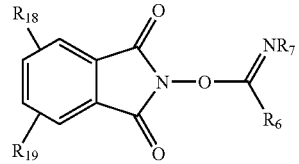
(IIb)

wherein $R_{12}$ and $R_{13}$ each, independently of one another, are hydrogen or $C_1$-$C_8$alkyl or cyclohexyl, or $R_{12}$ and $R_{13}$ form together with the N atom to which they are attached a 5 or 6 membered ring, optionally interrupted by —NH—, —N($C_1$-$C_8$alkyl)- and/or —O-atoms, $R_{16}$ and $R_{17}$ each, independently of one another, are hydrogen, $C_1$-$C_8$alkyl, cyclohexyl, benzyl, phenyl, halogen, OH, $C_1$-$C_8$alkoxy, $C_1$-$C_8$alkylthio, carboxy, $C_1$-$C_8$alkoxy-carbonyl, carbamoyl (C(O)NH$_2$), $C_1$-$C_8$alkylcarbamoyl, di-$C_1$-$C_8$alkylcarbamoyl, $C_1$-$C_8$acyl, nitro, amino, $C_1$-$C_8$alkylamino or di-$C_1$-$C_8$alkylamino;

$R_7$ $C_1$-$C_8$alkyl, cyclohexyl, benzyl, phenyl;

$R_6$ $C_1$-$C_8$alkyl, cyclohexyl, benzyl, phenyl;

$R_{18}$ and $R_{19}$ each, independently of one another, are hydrogen, $C_1$-$C_8$alkyl, cyclohexyl, benzyl, phenyl, halogen, OH, $C_1$-$C_8$alkoxy, $C_1$-$C_8$alkylthio, carboxy, $C_1$-$C_8$alkoxycarbonyl, carbamoyl (C(O)NH$_2$), $C_1$-$C_8$alkylcarbamoyl, di-$C_1$-$C_8$alkylcarbamoyl, $C_1$-$C_8$acyl, nitro, amino, $C_1$-$C_8$alkylamino or di-$C_1$-$C_8$alkylamino.

Preparation of the Compounds

The above-described compounds of the formula (I) or (II) can be prepared by methods known per se.

Compounds of the formula (I) can be prepared as described in U.S. Pat. No. 2,872,450 by reaction of cyclic oximides and thiocarboxylic acid ester chlorides according to the following scheme:

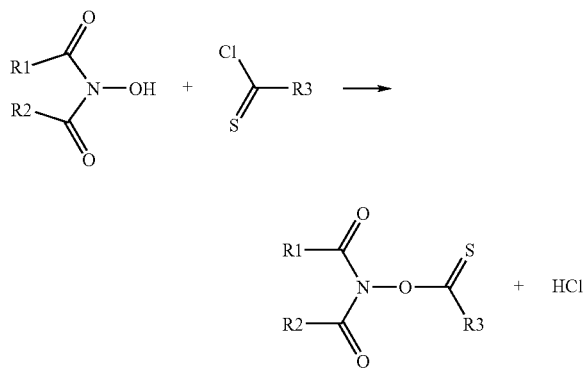

A further preparation route is the reaction of thiophosgene with a N-hydroxyimide obtaining a thiocarboxylic acid chloride which is further reacted with an amine or an alcohol according to the following scheme:

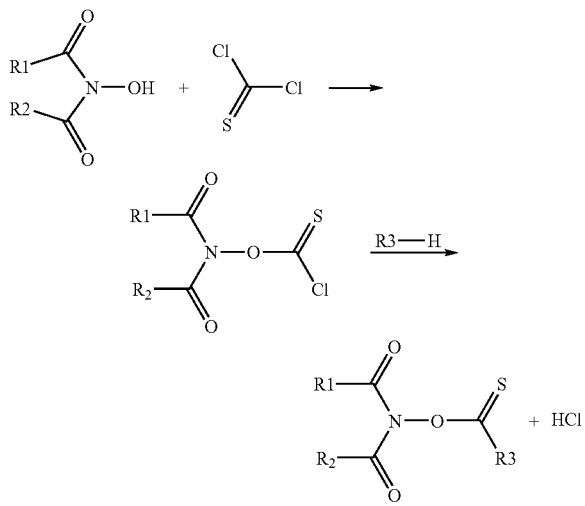

Compounds of the formula (II) may be prepared reacting an N-hydroxyimide or a salt thereof with an imide chloride according to the following scheme:

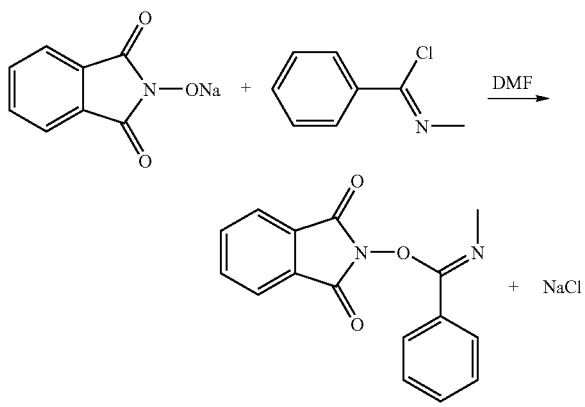

The imide chloride may be prepared as described in J. C. S. Perkin II, 1318 (1980).

The above referenced preparation routes are only examples, other routes may be possible.

Suitable dicarboxylic acids include, for example, succinic acid, $C_1$-$C_{18}$ alkylsuccinic acid, $C_2$-$C_{18}$ alkenylsuccinic acid, maleic acid, dimethylmaleic acid, glutaric acid, thioglycolic acid, imido diacetic acid, citric acid, 5-norbornene-2,3-dicarboxylic acid, 3,6-epoxy-1,2,3,6-tetrahydrophthalic acid, phthalic acid, substituted phthalic acid (halogen, COOR, nitro etc, as defined above) homophthalic acid, tetrahydrophthalic acid, hexahydrophthalic acid, 1,8-naphthalene dicarboxylic, pyridine-2,3-dicarboxylic acid, naphthalene-1,4,5,8-tetracarboxylic acid, 3,4,9,10-perylene tetracarboxylic acid, bicyclo[2.2.2]oct-7-ene-2,3,5,6-tetracarboxylic acid.

Use

The N-substituted imides may be used as polymerization initiators, especially as thermal radical initiators (TRI) in a curing agent for coatings that cure by free radical polymerisation. The coating may be a thermal curable coating composition, a double- (thermal and UV radiation) curable coating composition or a dual-(thermal curable) coating composition comprising at least a second crosslinkable resins. The thermal curing is carried out using NIR-curing or IR-curing or convection heat. It is also possible to use microwave heating. The double curing composition comprises in addition to the thermal initiator a photoinitiator. The double curing is carried out using NIR-curing or IR-curing followed by UV-curing or vice versa.

The invention further relates to thermal curable coating composition, comprising
a) at least an ethylenically unsaturated compound;
b) a thermal initiator effective to enable IR-curing or NIR-curing or to enable microwave curing or to enable ultrasound curing or to enable the convection heat curing of the ethylenically unsaturated compound, wherein the thermal initiator is a N-substituted imide of the formula (I) and/or (II).

The invention further relates to a dual curable coating composition, comprising
a) at least an ethylenically unsaturated compound and a second thermal crosslinkable compound;
b) a thermal initiator effective to enable IR-curing or NIR-curing or to enable microwave curing or to enable ultrasound curing or to enable the convection heat curing of the ethylenically unsaturated compound, wherein the thermal initiator is a N-substituted imide of the formula (I) and/or (II).

The invention further relates to a double (thermal and UV) curable coating composition, comprising
a) at least an ethylenically unsaturated compound;
b) a thermal initiator effective to enable IR-curing or NIR-curing curing or to enable microwave curing or to enable ultrasound curing or to enable the convection heat curing of the ethylenically unsaturated compound, wherein the thermal initiator is a N-substituted imide of the formula (I) and/or (II);
c) a photoinitiator effective to enable UV-curing of the ethylenically unsaturated compound.

Definitions:

Thermal Curing:

Thermal curing refers to the application of convection heat or IR- or NIR-radiation or microwave irradiation or ultrasound exposure after the mixture has been applied to substrate. In case of powder coatings the adhered powder coating is first melted to form a surface layer preferably by convection heat. Suitable temperatures to initiate and complete free-radical polymerization are 60-180° C.

NIR-Curing

The NIR radiation used in the process according to the invention is short-wave infrared radiation in the wavelength range from about 750 nm to about 1500 nm, preferably 750 nm to 1200 nm. Radiation sources for NIR radiation include, for example, conventional NIR radiation emitters, which are available commercially (for example, from Adphos).

IR-Curing

The IR radiation used in the process according to the invention is medium wave radiation in the wave length range from about 1500 nm to about 3000 nm and/or longer-wave infrared radiation in the wave length range above 3000 nm.

IR radiation emitters of this kind are available commercially (for example, from Heraeus).

Microwave Curing:

The microwave radiation used in this process according to the invention is electro magnetic radiation in the wavelength range from about 1 mm to 30 cm.

Ultrasound Curing:

Ultrasound used in this process according to the invention is sound with a frequency above 20 kHz.

UV-Curing

The photochemical curing step is carried out usually using light of wavelengths from about 200 nm to about 600 nm, especially from 200 to 450 nm. As light sources there are used a large number of the most varied types. Both point sources and planiform projectors (lamp carpets) are suitable. Examples are: carbon arc lamps, xenon arc lamps, medium-, high- and low-pressure mercury lamps, optionally doped with metal halides (metal halide lamps), microwave-excited metal-vapor lamps, excimer lamps, super actinic fluorescent tubes, fluorescent lamps, argon filament lamps, electronic flash lamps, photographic flood lights, electron beams and X-rays generated by means of synchrotrons or laser plasma.

Double-Curing

Double curable systems comprise ethylenically unsaturated monomers, which can be polymerized by UV radiation or which can be polymerized thermally induced by IR or NIR radiation or microwave irradiation or ultrasound exposure or by convection heat. In a double cure system the thermal curing is preferably followed by UV-curing. However, it is also possible that the UV-curing follows the thermal curing.

Dual-Curing

Dual curable systems comprise ethylenically unsaturated monomers, which can be polymerized thermally induced by IR or NIR radiation or microwave irradiation or ultrasound exposure or by convection heat. Furthermore, at least one second thermal crosslinkable compound is present. The second compound preferably crosslinks via a polyol-isocyanate reaction to form a polyurethane.

Definition of the Ethylenically Unsaturated Compound

Suitable compounds with olefinic double bonds are all compounds that can be crosslinked by free radical polymerization of the double bond. The ethylenically unsaturated compound may be a monomer, an oligomer or a prepolymer, a mixture thereof or a copolymer thereof.

Monomers suitable for free-radical polymerization are, for example, ethylenically unsaturated polymerizable monomers selected from the group consisting of (meth)acrylates, alkenes, conjugated dienes, styrenes, acrolein, vinyl acetate, vinylpyrrolidone, vinylimidazole, maleic anhydride, fumaric anhydride, (meth)acrylic acid, (meth)acrylic acid derivatives such as esters and amides, vinyl halides and vinylidene halides. Preferred are compounds having (meth)acryloyl, vinyl and/or maleinate groups. Especially preferred are (meth)acrylates.

Compounds which contain free-radically polymerizable double bonds in the form of the preferred (meth)acryloyl groups may be produced in accordance with conventional methods. This may proceed, for example, by: transesterifying OH-functional resins, such as OH-functional polyesters, polyacrylates, polyurethanes, polyethers or epoxy resins, with alkyl esters of (meth)acrylic acid; esterifying the stated OH-functional resins with (meth)acrylic acid; reacting the stated OH-functional resins with isocyanate-functional (meth)acrylates; reacting acid-functional resins, such as polyesters, polyacrylates, polyurethanes with epoxy-functional (meth)acrylates; reacting epoxy-functional resins, such as polyesters, polyacrylates, epoxy resins with (meth)acrylic acid. These production methods stated by way of example are described in the literature and known to the person skilled in the art.

Examples of prepolymers or oligomers include (meth)acryloyl-functional (meth)acrylic copolymers, polyurethane (meth)acrylates, polyester (meth)acrylates, unsaturated polyesters, polyether (meth)acrylates, silicone (meth)acrylates and epoxy resin (meth)acrylates having number-average molecular masses from, for example, 500 to 10,000, preferably 500 to 5,000.

The (meth)acryloyl-functional prepolymers may be used in combination with reactive diluents, i.e., free-radically polymerizable low molecular weight compounds with a molar mass of below 500 g/mol. The reactive diluents may be mono-, di- or polyunsaturated. Examples of monounsaturated reactive diluents are (meth)acrylic acid and the esters thereof, maleic acid and the esters thereof, vinyl acetate, vinyl ether, substituted vinyl ureas, styrene, vinyltoluene. Examples of diunsaturated reactive diluents are di(meth)acrylates such as alkylene glycol di(meth)acrylate, polyethylene glycol di(meth)acrylate, 1,3-butanediol di-(meth)acrylate, vinyl(meth)acrylate, allyl(meth)acrylate, divinylbenzene, dipropylene glycol di(meth)acrylate, hexanediol di(meth)acrylate. Examples of polyunsaturated reactive diluents are glycerol tri(meth)acrylate, trimethylolpropane tri(meth)acrylate, pentaerythritol tri(meth)-acrylate, pentaerythritol tetra(meth)acrylate. The reactive diluents may be used alone or in mixture.

Suitable salts of acrylic acid or methacrylic acid are, for example, $(C_1-C_4alkyl)_4$ammonium or $(C_1-C_4alkyl)_3$NH salts, e.g. the tetramethylammonium, tetraethylammonium, trimethylammonium or triethylammonium salt, the trimethyl-2-hydroxyethylammonium or triethyl-2-hydroxyethylammonium salt, the dimethyl-2-hydroxyethylammonium or diethyl-2-hydroxyethylammonium salt.

The ethylenically unsaturated compounds may contain, in addition to the olefinic double bonds, one or more further, identical or different functional groups. Examples of functional groups include hydroxyl, isocyanate (optionally blocked), N-methylol, N-methylolether, ester, carbamate, epoxy, amino (optionally blocked), acetoacetyl, alkoxysilyl and carboxyl groups. Examples are polyurethane resins with (meth)acryloyl groups and glycerol mono- and di-(meth)acrylate, trimethylol propane mono- and di(meth)acrylate or pentaerythritol tri(meth)-acrylate.

Additives

The above-described compositions may further comprise customary additives, which may, as an alternative, also be added after the polymerization. Such additives can be added in small amounts, e.g. UV-absorbers or light stabilizers, e.g. compounds selected from the group consisting of hydroxyphenylbenzotriazoles, hydroxyphenylbenzophenones, oxalamides and hydroxyphenyl-s-triazines. Particularly suitable light stabilizers are those selected from the group consisting of N-alkoxy-Hals compounds such as Tinuvin 123, or of sterically hindered amines Hals compounds of the 2-(2-hydroxyphenyl)-1,3,5-triazine or 2-hydroxyphenyl-2H-benzotriazole type. Examples of light stabilizers of the 2-(2-hydroxyphenyl)-1,3,5-triazine type are known from the patent literature, e.g. U.S. Pat. No. 4,619,956, EP-A-434 608, U.S. Pat. No. 5,198,498, U.S. Pat. No. 5,322,868, U.S. Pat. No. 5,369,140, U.S. Pat. No. 5,298,067, WO-94/18278, EP-A-704 437, GB-A-2,297,091 or WO-96/28431. 3,3,5,5 polysubstituted morpholin-2-one derivatives as described in U.S. Pat. No. 6,140,326 are well established light stabilizers for coatings.

The compositions may further comprise other customary additives such as leveling agents, rheology-influencing agents, such as, fine-particle silicic acid, layer silicates, urea compounds; thickeners, e.g., based on partially cross-linked carboxy-functional polymers or polyurethanes; defoamers, wetting agents, anti-crater agents, degassing agents, e.g., benzoin, antioxidants.

The compounds may further comprise additives to improve the storage stability such as polymerization inhibitors on nitroxyl basis, e.g. Irgastab UV10 and 2,2,6,6-tetramethyl-4-hydroxy-piperidin-1-oxyl (4-hydroxy-TEMPO); or highly sterically hindered nitroxyl radicals or quinone methides as described in the European Patent application EO04104248.2, filed Sep. 3, 2004.

Any thermal initiator known in the art may be used in addition to the N-substituted imides Preferably, the additional thermal initiators are peroxides such as dialkyl peroxides, dicumyl peroxide, peroxo carboxylic acids and so one and azo initiators as disclosed in U.S. Pat. No. 5,922,473. The coating agents may be unpigmented coating agents, e.g., transparent clear coats or pigmented coating agents.

The coating agents may contain fillers and/or transparent, color- and/or special effect-imparting pigments and/or soluble dyes. Examples of inorganic or organic color-imparting pigments include titanium dioxide, micronized titanium dioxide, iron oxide pigments, carbon black, azo pigments, phthalocyanine pigments, quinacridone or pyrrolopyrrole pigments. Examples of special effect-imparting pigments include metallic pigments, e.g., of aluminum, copper or other metals; interference pigments, such as, metal oxide-coated metallic pigments, e.g., titanium dioxide-coated or mixed oxide-coated aluminum, coated mica, such as, titanium dioxide-coated mica and graphite special-effect pigments. Examples of suitable fillers include silica, aluminum silicate, barium sulfate, calcium carbonate and talc.

In double cure systems a photoinitiator is needed in addition to the thermal radical initiator. Suitable photoinitiators are known to those skilled in the art. For example, α-hydroxyketones and α-aminoketones, phenylglyoxalates or phospine oxides are photoinitiators commonly used in graphic arts applications.

Especially preferred are, for example, the following commercially available photoinitiators:

Darocur 1173: 2-hydroxy-2-methyl-1-phenyl-1-propanone (HMPP) and Oligomeric HMPP,
Irgacure 184: 1-hydroxy-cyclohexyl-phenylketone,
Irgacure 2959: 2-hydroxy-1-[4-(2-hydroxyethoxy)phenyl]-2-methyl-1-propanone,
Irgacure 369: 2-benzyl-2-(dimethylamino)-1-[4-(4-morpholinyl)phenyl]-1-butanone,
Irgacure 1300: Irgacure 369+Irgacure 651 (benzildimethylketal),
Irgacure 379: 2-(4-Methylbenzyl)-2-(dimethylamino)-1-[4-(4-morpholinyl)phenyl]-1-butanone,
Irgacure 127: 2-Hydroxy-1-{4-[4-(2-hydroxy-2-methyl-propionyl)-benzyl]-phenyl}-2-methylpropan-1-one,
Irgacure 754: oxo-phenyl-acetic acid 1-methyl-2-[2-(2-oxo-2-phenyl-acetoxy)-propoxy]-ethyl ester,
Irgacure 819: bis(2,4,6-trimethylbenzoyl)-phenylphosphine oxide,
Irgacur 250: 4-isobutylphenyl-4'-methylphenyl iodonium hexafluorophosphate,
Darocur ITX: 2-isopropylthioxanthone and 4-isopropylthioxanthone,
Darocur EDB: ethyl-4-dimethylamino benzoate,
Darocur EHA: 2-ethylhexyl-4-dimethylamino benzoate; or mixtures of the above photoinitiators.

The photopolymerisable compositions comprise the photoinitiator advantageously in an amount from 0.05 to 15% by weight, preferably from 0.1 to 8% by weight, based on the composition.

In dual curing systems at least one second thermal crosslinkable compound is present selected from 1. surface coatings based on cold- or hot-crosslinkable alkyd, acrylate, polyester, epoxy or melamine resins or mixtures of such resins, optionally with the addition of a curing catalyst;
2. two-component polyurethane surface coatings based on hydroxyl-group-containing acrylate, polyester or polyether resins and aliphatic or aromatic isocyanates, isocyanurates or polyisocyanates;
3. two-component polyurethane surface coatings based on thiol-group-containing acrylate, polyester or polyether resins and aliphatic or aromatic isocyanates, isocyanurates or polyisocyanates;
4. one-component polyurethane surface coatings based on blocked isocyanates, isocyanurates or polyisocyanates which are deblocked during stoving; the addition of melamine resins is also possible, if desired;
5. one-component polyurethane surface coatings based on aliphatic or aromatic urethanes or polyurethanes and hydroxyl-group-containing acrylate, polyester or polyether resins;
6. one-component polyurethane surface coatings based on aliphatic or aromatic urethane acrylates or polyurethane acrylates having free amine groups in the urethane structure and melamine resins or polyether resins, optionally with the addition of a curing catalyst;
7. two-component surface coatings based on (poly)ketimines and aliphatic or aromatic isocyanates, isocyanurates or polyisocyanates;
8. two-component surface coatings based on (poly)ketimines and an unsaturated acrylate resin or a polyacetoacetate resin or a methacrylamidoglycolate methyl ester;
9. two-component surface coatings based on carboxyl- or amino-group-containing polyacrylates and polyepoxides;
10. two-component surface coatings based on anhydride-group-containing acrylate resins and a polyhydroxy or polyamino component;
11. two-component surface coatings based on acrylate-containing anhydrides and polyepoxides;
12. two-component surface coatings based on (poly)oxazolines and anhydride-group-containing acrylate resins or unsaturated acrylate resins or aliphatic or aromatic isocyanates, isocyanurates or polyisocyanates;
13. two-component surface coatings based on unsaturated (poly)acrylates and (poly)-malonates;
14. thermoplastic polyacrylate surface coatings based on thermoplastic acrylate resins or extrinsically crosslinking acrylate resins in combination with etherified melamine resins;
15. surface-coating systems, especially clearcoats, based on malonate-blocked isocyanates with melamine resins (e.g. hexamethoxymethylmelamine) as crosslinkers (acid-catalysed);
16. UV-curable systems based on oligomeric urethane acrylates and/or acylate acrylates, optionally with the addition of other oligomers or monomers;
17. dual-cure systems, which are cured first thermally and then by UV, or vice versa, the constituents of the surface-coating formulation containing double bonds that can be caused to react by UV light and photoinitiators and/or by electron-beam curing.

The resulting coating materials of the invention may be conventional coating materials, containing organic solvents, aqueous coating materials, substantially or fully solvent-free and water-free liquid coating materials (100% systems), substantially or fully solvent-free and water-free solid coating materials (powder coating materials), or substantially or fully solvent-free powder coating suspensions (powder slurries).

Non limiting examples of suitable substrates are, for example, wood, textiles, paper, ceramics, glass, glass fibres, plastics such as polyester, polyethylene terephthalate, polyolefins or cellulose acetate, especially in the form of films, and also metals such as Al, Cu, Ni, Fe, Zn, Mg or Co and GaAs, Si or $SiO_2$.

The coating composition may also be an ink composition. Thus, the substrate is printed with an ink composition to form an ink film on the substrate.

The inventive compositions can be used for various purposes, for example as printing inks, such as screen printing inks, flexographic printing inks or offset printing inks, as clearcoats, gelcoats as colour coats, as white coats, e.g. for wood or metal, as powder coatings, as paints, inter alia for paper, water, metal or plastic, as daylight-curable coatings for marking buildings and roads, for photographic reproduction processes, for holographic recording materials, for image recording processes or for the production of printing plates which can be developed using, for example, organic solvents or aqueous-alkaline media, for the production of masks for screen printing, as dental filling materials, as adhesives, as pressure-sensitive adhesives, as laminating resins, as photoresists, e.g. galvanoresists, etch or permanent resists, both liquid and dry films, as photostructurable dielectrics, and as solder stopping masks for electronic circuits, as resists for the preparation of colour filters for any type of screen or for producing structures in the production process of plasma displays and electroluminescence displays, for the production of optical switches, optical gratings (interference gratings), for the preparation of three-dimensional objects by mass curing (UV curing in transparent moulds) or by the stereolithography process, as is described, for example, in U.S. Pat. No. 4,575,330, for the preparation of composite materials (e.g. styrenic polyesters which may contain glass fibres and/or other fibres and other auxiliaries) and other thick-layer materials, for the preparation of gel coats, for the coating or sealing of electronic components or as coatings for optical fibres. The compositions are also suitable for the preparation of optical lenses, e.g. contact lenses and Fresnel lenses, and for the preparation of medical instruments, auxiliaries or implants.

The compositions are also suitable for the preparation of gels having thermotropic properties. Such gels are described, for example, in DE 19700064 and EP 678534.

Furthermore, the compositions can be used in dry-film paints, as are described, for example, in Paint & Coatings Industry, April 1997, 72 or Plastics World, Volume 54, No. 7, page 48(5).

Preparation of the Coating

The components of the formulation and optionally further additives are applied uniformly to a substrate by means of known coating techniques, for example by spin-coating, immersion, knife coating, curtain pouring, brush application or spraying, especially by electrostatic spraying and reverse-roll coating, and also by electrophoretic deposition. The quantity applied (coat thickness) and the nature of the substrate (layer support) are dependent on the desired field of application. The range of coat thicknesses generally comprises values from 0.1 µm to 1 mm for gel coates and more than 1 mm for composites.

The invention further provides a process for curing a thermal curable coating composition comprising compounds of the formula I or II as thermal initiators and using IR-curing or NIR-curing or convection heat.

The invention further relates to a process for curing a coating composition which process comprises a) applying a coating layer onto a substrate, whereby the coating composition is a blend of at least an ethylenically unsaturated compound and an initiator of the formula I or II as defined above;

b) thermal curing of the applied coating layer.

The invention further relates to a process for double curing a coating composition which process comprises a) applying a coating layer onto a substrate, whereby the coating composition is a blend of at least an ethylenically unsaturated compound and an initiator of the formula I or II as defined above; and a photoinitiator as defined above;

b) thermal curing and UV-curing of the applied coating layer.

The invention further relates to a process for dual curing a coating composition which process comprises a) applying a coating layer onto a substrate, whereby the coating composition is a blend of at least an ethylenically unsaturated compound and a second thermal crosslinkable compound and an initiator of the formula I or II as defined above;

b) thermal curing of the applied coating layer.

EXAMPLES

Example 1

Preparation of N-methyl-benzimidic acid 1,3-dioxo-1,3-dihydro-isoindol-2-yl ester

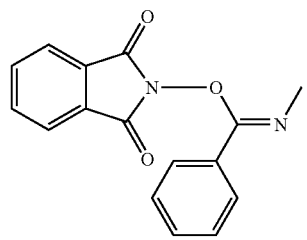

a) Preparation of N-Hydroxyphthalimide Sodium Salt 118 g (0.723 mol) of N-hydroxyphthalimide are suspended in 700 ml of ethanol absolute. To this suspension a solution of 16.65 g (0.723 mol) of sodium in 400 ml of ethanol absolute is added dropwise under stirring. The resulting red suspension is stirred for 19 h at room temperature. The so formed red solid is sucked off, washed with 100 ml of ethanol abs. and dried in vacuo to give 133 g of a red solid.

b) Preparation of the Title Compound

N-hydroxy phthalimide sodium salt (46.25 g.; 0.25 mol), is dissolved in dry DMF (220 ml), to the resulting suspension 38.8 g (0.25 mol) of N-methyl benzimidoyl chloride (prepared according to J. C. S. Perkin II, 1324, (1980)) are slowly added at room temperature, on stirring. The reaction mixture is stirred at room temperature for 19 h and then poured into 1.5 l of water. The so formed precipitate is sucked off and dried in vacuo to obtain 66.06 g of a a crude product which is then taken up in 250 ml of acetonitrile. After filtration 58.7 g of N-methyl-benzimidic acid 1,3-dioxo-1,3-dihydro-isoindol-2-yl ester are obtained in form of colorless crystals, mp. 174-176° C.

For C$_{16}$H$_{12}$N$_2$O$_3$ (280.29) calculated/found (%); C, 68.56/68.54; H, 4.32/4.49; N, 9.99/10.00.

Example 2

Preparation of N-ethyl-benzimidic acid 1,3-dioxo-1,3-dihydro-isoindol-2-yl ester

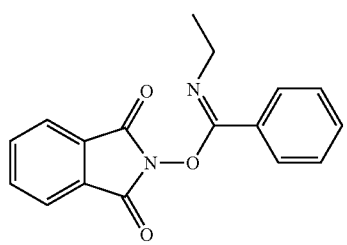

analogue to Example 1
colorless crystals; Yield 73%, mp. 124-126° C.
For C$_{17}$H$_{14}$N$_2$O$_3$ (294.31) calculated/found (%); C, 69.38/69.10; H, 4.79/4.63; N, 9.52/9.44.

Example 3

Preparation of N-butyl-benzimidic acid 1,3-dioxo-1,3-dihydro-isoindol-2-yl ester

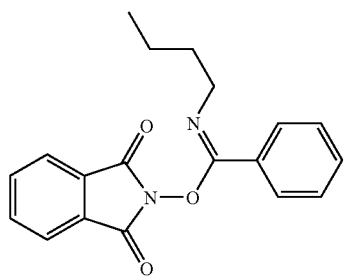

analogue to Example 1
colorless crystals; Yield 83%, mp. 42-45° C.
For C$_{18}$H$_{18}$N$_2$O$_3$ (322.37) Berechnet/Gefunden (%); C, 70.79/70.71; H, 5.63/5.64; N, 8.69/8.68.

Example 4

Preparation of N-methyl-benzimidic acid 2,5-dioxo-pyrrolidine-1-yl ester

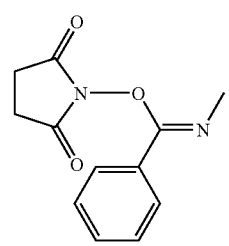

1.7 g (0.03 mol) of sodium methylate are added to a solution of 3.45 g (0.03 mol) of N-hydroxy succinimide in 25 ml of methanol. The reaction mixture is stirred for one h, concentrated under vacuo and the residue is taken up in 15 ml of DMF. 4.6 g (0.03 mol) of methyl benzimidoyl chloride are added on stirring. The reaction mixture is stirred at room temperature for 12 h and then poured into 120 ml of water. The so formed precipitate is sucked off and dried in vacuo to obtain 3.8 g of a crude product which is then taken up and recrystallised in 9 ml of toluene to give 3.05 g of N-methyl-benzimidic acid 2,5-dioxopyrrolidine-1-yl ester in form of colorless crystals; mp. 119-120° C.

For C$_{12}$H$_{12}$N$_2$O$_3$ (232.24) calculated/found (%); C, 62.06/61.85; H, 5.21/5.22; N, 12.06/12.00.

Example 5

Preparation of dimethyl-thiocarbamic acid O-(1,3-dioxo-1,3-dihydro-isoindol-2-yl) ester

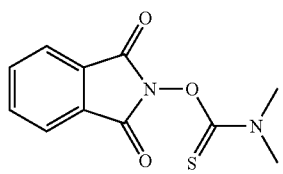

97.9 g (0.6 mol) of N-hydroxy phthalimide are added to 400 ml of pyridine. Then 76 g (0.615 mol) of dimethyl thiocarbamoyl chloride are added. The reaction mixture is stirred at room temperature for 21 h and then poured into 4 l of ice water. The so formed precipitate is sucked off and dried in vacuo to obtain 145 g of a a crude product which is then taken up and recrystallised in dichloromethane-hexane to give 127 g of dimethyl-thiocarbamic acid O-(1,3-dioxo-1,3-dihydro-isoindol-2-yl) calculated/found (%); C, 52.79/52.68; H, 4.03/4.14; N, 11.19/11.14.

Example 6

Preparation of dimethyl-thiocarbamic acid O-(1,3-dioxo-benzoisochinoline-2-yl) ester

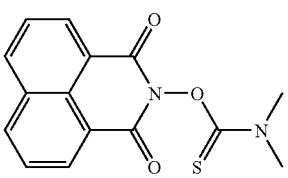

analogue to Example 5 using N-hydroxy-1,8-naphthalimide.
colorless crystals; Yield: 33%, mp. 185-190° C.
1H-NMR (CDCl$_3$, 300 MHz, ppm): 8.67 (d, J=7.5 Hz, 2ArH), 8.28 (d, J=7.5 Hz, 2ArH), 7.82 (t, J=7.5 Hz, 4 ArH), 3.51 (s, 2×CH$_3$).

Example 7

Preparation of dimethyl-thiocarbamic acid O-(2,5-dioxo-pyrrolidine-1-yl) ester

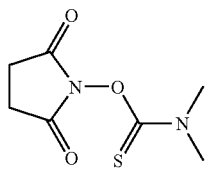

colorless crystals; Yield: 68.5%, mp. 148-151° C.
Calculated/found $C_7H_{10}N_2O_3S$ (202.23), (%); C, 41.57/41.61; H, 4.98/4.91; N, 13.85/13.76.

Example 8

Preparation of dimethyl-thiocarbamic acid —O-(1,3-dioxo-octahydro-isoindol-2-yl) ester

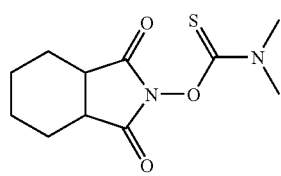

To a solution of 25.38 g (0.15 mol) of N-hydroxy-hexahydrophthalimide (prepared as described in Chem. Pharm. Bull., 16, (1968), 622) and 0.5 g 4-dimethylaminopyridine in 100 ml pyridine were added 18.54 g (0.15 mol) of dimethylthiocarbamoyl chloride. The mixture was stirred at room temperature during 3 h and then poured into 1000 ml of ice water. The precipitate was filtered off and recrystallized from 120 ml of ethanol to give 28.38 g of white crystals, mp. 124-126° C.

Infusion MS, for $C_{11}H_{16}N_2O_3S$ (256.33) found $[M+1]^+=257.1$.

Example 9

Preparation of N—(N',N'-dimethyl-thionocarbamoyl-oxy)-5-norbornene-2,3-dicarboximide

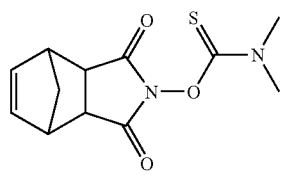

This compound was prepared in analogy to example 8 starting from 26.9 g (0.15 mol) of N-hydroxy-5-norbornene-2,3-dicarboximide (prepared as described in Bull. Soc. Chim. Fr., (1976), 833). Yield 36.3 g of colorless crystals after recrystallization from dichloromethaneacetonitrile, mp. 215-218° C.

Elemental analysis, for $C_{12}H_{14}N_2O_3S$ calcd./found (%): C, 54.12/54.18; H, 5.30/5.37; N, 10.52/10.52.

Example 10

Preparation of dimethyl-thiocarbamic acid O-(3,4-dimethyl-2,5-dioxo-2,5-dihydro-pyrrol-1-yl) ester

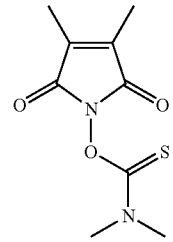

This compound was prepared in analogy to example 8 starting from 21.17 g (0.15 mol) of N-hydroxy-3,4-dimethyl-2,5-dioxo-2,5-dihydro-pyrrole (prepared as described in J. Chem. Soc., (1955), 631). Yield 23.50 g after recrystallization from ethanol, mp. 135-138° C. Infusion MS, for $C_9H_{12}N_2O_3S$ (228.27) found $[M+1]^+=229.1$

Example 11

Preparation of diisopropyl-thiocarbamic acid —O-(1,3-dioxo-1,3-dihydro-isoindol-2-yl) ester

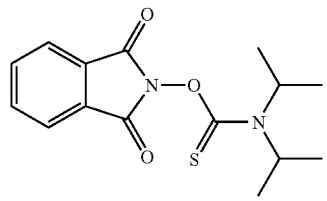

This compound was prepared in analogy to example 8 starting from 32.35 g (0.18 mol) of diisopropyl-thiocarbamoyl chloride (prepared as described in (Chem. Ber., 101, (1968), 113) and N-hydroxyphthalimide. Yield 21.44 g of white crystals after recrystallization from hexane, mp. 73-75° C.

$^1$H-NMR (300 MHz, $CDCl_3$): 7.94-7.89 (m, 2ArH), 7.82-7.78 (m, 2ArH), 5.29-5.26 (m, 1H), 3.89-3.86 (m, 1H), 1.59 (d, 6H), 1.32 (d, 6H).

Example 12

Preparation of dicyclohexyl-thiocarbamic acid —O-(1,3-dioxo-1,3-dihydro-isoindol-2-yl) ester

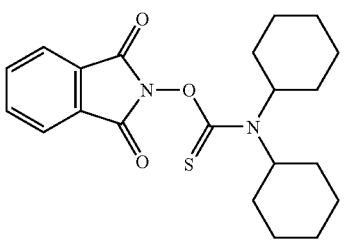

This compound was prepared in analogy to example 8 starting from 24.94 g (0.096 mol) of dicyclohexyl-thiocarbamoyl chloride (prepared as described in (Chem. Ber., 101, (1968), 113) and N-hydroxyphthalimide. Yield 9.65 g of white crystals after recrystallization from hexane, mp. 148-150° C.

AP-CI (butane) MS, for $C_{21}H_{26}N_2O_3S$ (386.51) found $[M+1]^+$=386.87

Application Examples

Curing Under NIR-Irradiation

Screening Formulation:

| % Weight | Product | Description | Supplier |
| --- | --- | --- | --- |
| 89 | Ebecryl 604 | Bisphenol-A epoxy diacrylate 80% in HDDA | UCB |
| 10 | Sartomer SR344 | Polyethylene glycol (400) diacrylate | Cray Valley |
| 1 | Ebecryl 350 | Silicone diacrylate | UCB |

Components were stirred until homogenous.

Tested Samples:
Compound of Example 5 and of Example 7.
1.00 g of the test compound was dissolved in 50.00 g of Screening Formulation using a tooth wheel dissolver for 30 min.

Application and Curing Conditions:
Coating was applied on steel panels using a slit coater (WFT 90 μm).
Curing under NIR-Lamps, with main emission between 750-1500 nm (eg. by Adphos) at 65% power output, distance to substrate 3 cm, line speed 3 m/min.

Testing Methods:
Pendulum Hardness (Koenig) according to DIN EN ISO 1522
Cross Hatch Test according to DIN 53 151

Results:

| Sample | Pendulum Hardness [s] | Cross Hatch |
| --- | --- | --- |
| EX. 5 | 207.2 | 1 |
| Ex. 7 | 207.2 | 0 |

Oven Curing:

| parts by wt | |
| --- | --- |
| 44.5 | Ebecryl 284 UCB Chemicals (88 parts aliphatic urethane acrylate/12 parts hexane diol diacrylat) |
| 32.2 | Roskydal UA VP LS 2308 (aliph. urethane tri/tetraacrylate) Bayer |
| 10 | TMPTA trimethylolpropyl triacrylate |
| 10 | TPGDA triprogyleneglycol diacrylate |
| 0.5 | Glide 100 (Flow agent Tego Chemicals) |

0.4 g of the compound of the compounds of Example 5, 10, 11 or 12 (see Table below) were dissolved in 20.00 g Screening Formulation using a magnet stirring device for 30 min. The mixture is applied to white coil-coat aluminum. The sample is baked in an oven at 160° C. for 30 min and a tack free dry film with a thickness of approximately 25 μcm is obtained. 45 Minutes after cure, the pendulum hardness according to König (DIN 53157) is measured.

| Example | Pendulum hardness in s |
| --- | --- |
| 5 | 126 |
| 10 | 133 |
| 11 | 137 |
| 12 | 137 |

Storing Stability:

Screening Formulation:

| % Weight | Product | Description | Supplier |
| --- | --- | --- | --- |
| 59.5 | Ebecrl 4858 | aliphatic urethane acrylate | UCB |
| 22.5 | HDDA | reactive diluent | UCB |
| 13 | TPGDA | reactive diluent | UCB |
| 0.5 | Byk 300 | surface active silicone additive | BYK Chemie |

Components were stirred until homogenous.

Tested Samples:
Compounds of Ex. 5, 7, 9, 10 and 12
1.00 g were dissolved in 50.00 g Screening Formulation using a magnet stirring device for 30 min.

Testing Methods:
Measurement of viscosity on ICI Cone Plate Viscosimeter at 20° C.

Storing Stability Initially after sample preparation viscosity was measured. Samples were split and stored in closed containers at 40° C. After a period of 4 weeks and 12 weeks, viscosity was measured again. As reference the screening formulation was treated and measured accordingly.

Results:

| | Viscosity [mPa s] | | |
| --- | --- | --- | --- |
| Sample | Initial value | 4 weeks 40° C. | 12 weeks 40° C. |
| Screening formulation | 300 | 280 | 230 |
| Ex. 5 | 340 | 310 | 260 |
| Ex. 7 | 360 | 320 | 260 |
| Ex. 9 | 240 | 280 | 280 |
| Ex. 10 | 250 | 240 | 320 |
| Ex. 12 | 250 | 260 | 140 |

Dual Curing 0.26 g of the compound of Ex. 5 were dissolved in 13.4 g Component A using a magnet stirring device for 30 min Subsequent component B is added and well homogenised

| parts by wt | Component A |
|---|---|
| 11.38 | Desmophen A 870, Bayer AG (hydroxyl functional polyacrylate 70% in butylacetate) |
| 21.23 | Desmophen VP LS 2089 (polyesterpolyol 75% in butylacetate) Bayer |
| 0.55 | Byk 306 (Flow agent) Byk Chemie |
| 32.03 | Methanol |
| | Component B |
| 32.09 | Roskydal UA VP LS 2337, Bayer AG (isocyanat functional urethane acrylate) |

The mixtures were applied to white coil-coat aluminum, air-dried for 5 minutes at room temperature a heated in an oven at 160° C. for 30 minutes. A tack free dry film with a thickness of approximately 40 μcm is obtained. 45 Minutes after cure, the pendulum hardness according to König (DIN 53157) is measured. Pendulum Hardness 140s.

Double Curing 0.4 g of a compound of Ex. 5 and 0.4 g Irgacure 184 were dissolved in 20.00 g Screening Formulation using a magnet stirring device for 30 min

| parts by wt | |
|---|---|
| 44.5 | Ebecryl 284 (88 parts aliphatic urethaneacrylate/12 parts Hexandioldiacrylat) UCB Chemicals |
| 32.2 | Roskydal UA VP LS 2308 (aliph. Urethane tri/tetraacrylate) Bayer AG |
| 10 | TMPTA Trimethylolpropyltriacrylate |
| 10 | TPGDA Triprogylenglycoldiacrylate |
| 0.5 | Glide 100 (Flow agent Tego Chemicals) |

The mixture is applied to white coil-coat aluminum. Irradiation is carried out using a UV-processor (2×120 W/cm) Mercury medium pressure Lamps at a belt speed of 5 m/min. The sample is baked in an oven at 160° C. for 30 min and a tack free dry film with a thickness of approximately 25 μm is obtained.

45 Minutes after cure, the pendulum hardness according to König (DIN 53157) is measured. Pendulum Hardness 146s.

The invention claimed is:

1. Compounds of the formula Ia and IIa

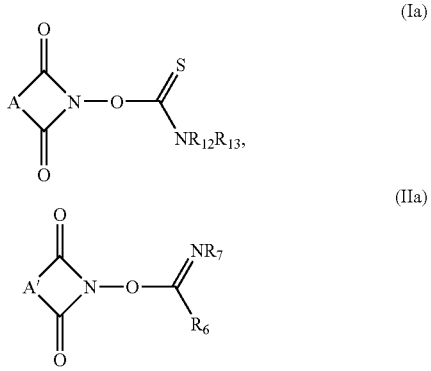

wherein

A is unsubstituted ethylene or propylene, ethylene or propylene substituted by $C_1$-$C_{18}$alkyl, $C_6$-$C_{14}$aryl, aralkyl, $C_5$-$C_{12}$cycloalkyl, halogen, OH, $C_1$-$C_{18}$alkoxy, $C_1$-$C_{18}$alkylthio, carboxy, $C_1$-$C_{18}$alkoxycarbonyl, carbamoyl (C(O)NH$_2$), $C_1$-$C_{18}$alkylcarbamoyl, di-$C_1$-$C_{18}$alkylcarbamoyl, acyl, nitro, amino, $C_1$-$C_{18}$alkylamino or di-$C_1$-$C_{18}$alkylamino; or A is —CH$_2$—X—CH$_2$— wherein X is O, NH, N($C_1$-$C_{18}$alkyl); or —N(OH)—CO—N(OH)—; or A together with the adjacent —CO—N—CO— group may form a bicyclic or polycyclic ring, said ring having up to 20 non hydrogen atoms, and wherein said ring may contain the structural element

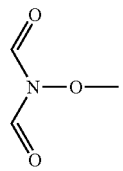

more than once;

$R_{12}$ and $R_{13}$ independently of one another are hydrogen, $C_1$-$C_{18}$alkyl, cyclohexyl, phenyl, benzyl, or $R_{12}$ and $R_{13}$ form together with the N atom to which they are attached a 5 or 6 membered ring, optionally interrupted by —NH—, —N($C_1$-$C_8$alkyl)-, —O— and/or S-atoms, A' is unsubstituted ethylene or propylene, ethylene or propylene substituted by $C_1$-$C_{18}$alkyl, $C_6$-$C_{14}$aryl, aralkyl, $C_5$-$C_{12}$cycloalkyl, halogen, OH, $C_1$-$C_{18}$alkoxy, $C_1$-$C_{18}$alkylthio, carboxy, $C_1$-$C_{18}$alkoxycarbonyl, carbamoyl (C(O)NH$_2$), $C_1$-$C_{18}$alkylcarbamoyl, di-$C_1$-$C_{18}$alkylcarbamoyl, acyl, nitro, amino, $C_1$-$C_{18}$alkylamino or di-$C_1$-$C_{18}$alkylamino; or A' is —CH$_2$—X—CH$_2$— wherein X is O, NH, N($C_1$-$C_{18}$alkyl); or —N(OH)—CO—N(OH)—; or A' together with the adjacent —CO—N—CO— group may form a bicyclic or polycyclic ring, said ring having up to 20 non hydrogen atoms, and wherein said ring may contain the structural element

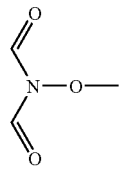

more than once;

$R_6$ is hydrogen, $C_1$-$C_{18}$alkyl, cyclohexyl, phenyl, benzyl, $NR_{14}R_{15}$; wherein $R_{14}$ and $R_{15}$ independently of one another are hydrogen, $C_1$-$C_{18}$alkyl, cyclohexyl, phenyl or $R_{14}$ and $R_{15}$ form together with the N atom to which they are attached a 5 or 6 membered ring, optionally interrupted by —NH—, —N($C_1$-$C_8$alkyl)-, —O— and/or S-atoms, $R_7$ is hydrogen, $C_1$-$C_{18}$alkyl, cyclohexyl, phenyl, benzyl; or $R_7$ and $R_{14}$ or $R_7$ and $R_{15}$ form together with the N-atom attached to $R_7$ a 5-6 membered ring, optionally interrupted by —NH—, —N($C_1$-$C_8$alkyl)-, —O— and/or S-atoms.

2. Compounds according to claim 1, of the formula Ib and IIb

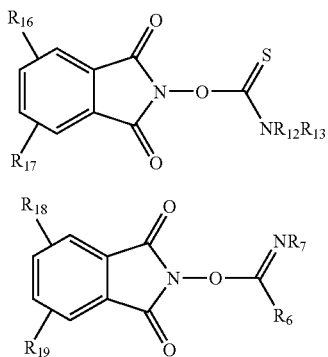
(Ib)

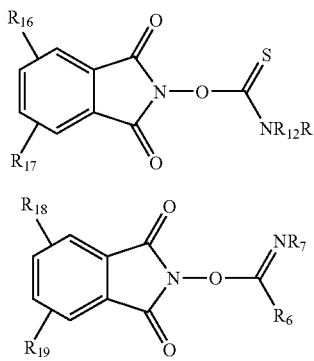
(IIb)

wherein $R_{12}$ and $R_{13}$ each, independently of one another, are hydrogen or $C_1$-$C_8$alkyl or cyclohexyl, or $R_{12}$ and $R_{13}$ form together with the N atom to which they are attached a 5 or 6 membered ring, optionally interrupted by —NH—, —N($C_1$-$C_8$alkyl)- and/or —O-atoms, $R_{16}$ and $R_{17}$ each, independently of one another, are hydrogen, $C_1$-$C_8$alkyl, cyclohexyl, benzyl, phenyl, halogen, OH, $C_1$-$C_8$alkoxy, $C_1$-$C_8$alkylthio, carboxy, $C_1$-$C_8$alkoxycarbonyl, carbamoyl (C(O)NH$_2$), $C_1$-$C_8$alkylcarbamoyl, di-$C_1$-$C_8$alkylcarbamoyl, $C_1$-$C_8$acyl, nitro, amino, $C_1$-$C_8$alkylamino or di-$C_1$-$C_8$alkylamino;

$R_7$ is $C_1$-$C_8$alkyl, cyclohexyl, benzyl or phenyl;

$R_6$ is $C_1$-$C_8$alkyl, cyclohexyl, benzyl or phenyl;

$R_{18}$ and $R_{19}$ each, independently of one another, are hydrogen, $C_1$-$C_8$alkyl, cyclohexyl, benzyl, phenyl, halogen, OH, $C_1$-$C_8$alkoxy, $C_1$-$C_8$alkylthio, carboxy, $C_1$-$C_8$alkoxycarbonyl, carbamoyl (C(O)NH$_2$), $C_1$-$C_8$alkylcarbamoyl, di-$C_1$-$C_8$alkylcarbamoyl, $C_1$-$C_8$acyl, nitro, amino, $C_1$-$C_8$alkylamino or di-$C_1$-$C_8$alkylamino.

3. Compounds according to claim 1, wherein A and A' independently are phenylene, cyclohexylene, cyclohexenylene, 1,8-naphthylene or pyridinylene.

4. Compounds according to claim 1, wherein A and A' independently are ethylene or propylene or ethylene or propylene substituted $C_1$-$C_4$alkyl.

5. A thermally curable coating composition, comprising
   a) at least an ethylenically unsaturated compound;
   b) a thermal initiator effective to enable IR-curing or NIR-curing or to enable microwave curing or to enable ultrasound curing or to enable the convection heat curing of the ethylenically unsaturated compound, wherein the thermal initiator is a N-substituted imide of the formula (Ia) and/or (IIa) according to claim 1.

6. A dual curable coating composition, comprising
   a) at least an ethylenically unsaturated compound and a second thermal crosslinkable compound;
   b) a thermal initiator effective to enable IR-curing or NIR-curing or to enable microwave curing or to enable ultrasound curing or to enable the convection heat curing of the ethylenically unsaturated compound, wherein the thermal initiator is a N-substituted imide of the formula (Ia) and/or (IIa) according to claim 1.

7. A double curable coating composition, comprising
   a) at least an ethylenically unsaturated compound;
   b) a thermal initiator effective to enable IR-curing or NIR-curing or to enable microwave curing or to enable ultrasound curing or to enable the convection heat curing of the ethylenically unsaturated compound, wherein the thermal initiator is a N-substituted imide of the formula (Ia) and/or (IIa) according to claim 1;
   c) a photoinitiator effective to enable UV-curing of the ethylenically unsaturated compound.

* * * * *